United States Patent [19]

Munk

[11] 3,934,456
[45] Jan. 27, 1976

[54] SOLVENT GRADIENT GENERATOR FOR CHROMATOGRAPHY SYSTEMS

[75] Inventor: Miner N. Munk, Walnut Creek, Calif.

[73] Assignee: Varian Associates, Palo Alto, Calif.

[22] Filed: July 22, 1974

[21] Appl. No.: 490,549

[52] U.S. Cl............ 73/61.1 C; 210/198 C; 417/536
[51] Int. Cl.²........................................ G01N 31/08
[58] Field of Search.......... 73/61.1 C; 417/534, 535, 417/536; 210/198 C

[56] References Cited
UNITED STATES PATENTS

| | | | |
|---|---|---|---|
| 505,090 | 9/1893 | Carse.................... | 417/536 |
| 1,498,471 | 6/1924 | Miller..................... | 417/536 X |
| 2,670,683 | 3/1954 | Lundh..................... | 417/536 |
| 3,446,057 | 5/1969 | Bakalyar et al............. | 73/61.1 C X |
| 3,507,580 | 4/1970 | Howard et al................. | 417/536 X |
| 3,701,609 | 10/1972 | Bailey...................... | 73/61.1 C X |
| 3,830,369 | 8/1974 | Pfadenhauer.................. | 210/198 C |

FOREIGN PATENTS OR APPLICATIONS

| | | | |
|---|---|---|---|
| 701,252 | 1/1965 | Canada............................. | 73/61.1 C |

Primary Examiner—Richard C. Queisser
Assistant Examiner—Joseph W. Roskos
Attorney, Agent, or Firm—Stanley Z. Cole; Gerald M. Fisher; John J. Morrissey

[57] ABSTRACT

Solvent gradient generating apparatus in a liquid column chromatography system. A multi-compartment vessel having an input/output port pair for each compartment is coupled between a high pressure pump and the column cell for providing both gradient generation and pulse damping. A piston, which is slidably contained within the vessel, sealably provides the compartments. Means external to the vessel are provided for controlling the rate of movement of the piston within the vessel. The volume of each compartment is controlled by the position of the piston, and the rate of movement of the piston controls mixing of the solvent components delivered to the column cell. Each compartment has input and output ports. In one embodiment, both input ports are coupled to the high pressure pump while only one output port is coupled to the column cell. In another embodiment, only one input port is coupled to the pump and the other input port and one output port are sealed.

22 Claims, 3 Drawing Figures

SOLVENT GRADIENT GENERATOR FOR CHROMATOGRAPHY SYSTEMS

BACKGROUND OF THE INVENTION

1. Field of the Invention

This invention relates, in general, to apparatus for precisely mixing liquids in high pressure systems and, more particularly, relates to solvent gradient generating apparatus in liquid chromatography systems.

Liquid chromatography pertains to a particular variety of equipment and techniques for analyzing the components of an unknown sample of liquid material, qualitatively and/or quantitatively. According to one liquid chromatographic system, a column cell is provided having a stationary liquid contained therein such that an immiscible mobile liquid percolates or flows therethrough. Such a liquid/liquid chromatography system may be characterized as a partition or solution system. The sample is retained by partitioning between the mobile liquid and the stationary liquid.

In another liquid chromatographic system, the column contains a solid instead of a stationary liquid. Such a system may be characterized as an absorption chromatography system. The mobile liquid is propelled through the solid absorbents, and variations in properties of the substance emerging from the column are detected and plotted.

In chromatography systems, mobile liquid flow rates and volumes must be precisely controlled if accurate analysis is to result. Constant flow rate systems are utilized for minimizing adverse affects of changes in uncontrolled variables on the constancy of the volumetric flow rate. Two primary classes of pumps are utilized in a constant flow rate system. A displacement type pump expels fluid contained within a limited reservoir by a piston under pressure. A displacement type pump advantageously provides nonpulsating flow, but provides only a limited amount of liquid due to its finite capacity. A reciprocating type pump, however, provides an unlimited reservoir and therefore an unlimited amount of liquid; but its flow is undesirably pulsating. Pulse damping apparatus must accompany reciprocating pump systems because detectors are usually flow rate sensitive. Detector noise levels are often determined by short term pulsations in flow from these reciprocating pumps. However, pulsating pumps are less expensive than displacement type pumps. It is therefore economically desirable to utilize the pulsating type pumps in combination with pulse damping apparatus.

Several pumping schemes have been proposed whereby solutions are mixed in precise amounts with respect to time. One proposed gradient generator utilizes a pair of high pressure displacement pumps which dispels fluid into a common conductor, such as a tee or mixing chamber, at controlled rates. Such a system however requires two high pressure pumps and is therefore relatively expensive.

Another pumping system heretofore proposed utilizes a first high pressure pump propelling its solvent into a second high pressure pump where the solvent is stirred with the contents of the second pump. The second pump acts as a variable volume mixing chamber to provide the desired mixture. As with the proposed system described above, a pair of expensive high pressure pumps is required.

Another proposed pumping system utilizes a low pressure metering pump dispelling its liquid into a calibrated volume of solvent of different composition. The mixture of solvent initially in the calibrated volume with liquid pumped in by the low pressure metering pump forms the feed solvent for the high pressure pump. The high pressure pump must have a small hold-up volume. Low hold-up volume, high pressure pumps are of the reciprocating type. An undesirably pulsating flow to the column is provided, unless pulse damping apparatus is supplied. Accordingly not only are two pumps required, but damping apparatus is also required.

Still another contemporary pumping arrangement in chromatography systems use a single high pressure pump in combination with a storage coil, a mixing tee, and a pair of solenoid valves coupled to the mixing tee. Each solenoid valve is alternately pulsed into the open position, and the relative time for each of the valves to open determines the mixture of the final solution delivered into the mixing tee. However, such pulse solenoid valves typically exhibit a relatively short life cycle. Furthermore, certain liquid combinations pose an unacceptable mixing problem at the mixing tee when passing through the valves. Still further, because such a system mixes the two components in the storage coil, part of the liquid solvent at the interface between the two components must be discarded.

It is therefore a general object of the present invention to provide an improved low-cost, high-pressure and constant volume flow rate solvent gradient generator in a chromatography system.

SUMMARY OF THE INVENTION

The present invention overcomes the drawbacks of the prior art by providing solvent gradient generating apparatus in a liquid chromatography system which includes an enclosed vessel having a plurality of compartments. A piston is slidably contained within the vessel to sealably provide, in combination with the bore of the vessel, the compartments having varying volumes as controlled by movement of the piston. Each compartment has a pair of input and output ports, selected ones of which are sealed in accordance with particular system application.

A first embodiment provides a high pressure pump coupled to commonly provide a first liquid solvent to each input port. A first compartment has the piston displaced to provide less volume than that of the second compartment, and the output port of the first compartment is sealed. The second compartment has contained therein a second liquid solvent which is to be mixed with the first solvent in precise proportions. Upon movement of the piston at a predetermined rate to increase the volume of the first compartment and to decrease the volume of the second compartment, the first liquid solvent is mixed and in the second compartment with the second liquid solvent in the desired proportions, and the mixture is output from the second compartment to a chromatographic column. Stirring means are included in the second compartment for agitating the mixture.

A feature of the first embodiment is a low pressure seal circumscribing the piston in a manner contiguous with the vessel for separating the compartments and thereby retaining purity of the first solvent in the first compartment. Because substantially equal pressures are provided on opposing sides of the piston head, a low pressure seal suffices instead of a more expensive high pressure seal.

Another embodiment of the present invention couples the above described multi-compartmented vessel with a high pressure pump such that the pump is coupled to input a first liquid solvent into only one input port. The piston is initially displaced to minimize the first compartment's volume so as to provide a larger volume in the second compartment which is filled with a second liquid solvent. The high pressure pump outlet is also coupled to a mixing chamber such that its flow divides into the first compartment and into the mixing chamber. The output port of the second compartment is coupled to the mixing chamber such that, upon displacement of the piston at a controlled rate in a direction to force fluid from the second compartment, precise amounts of second solution and first solution are input into the mixing chamber.

A low pressure seal circumscribing the piston within the enclosed vessel is also a feature of the second embodiment, similar to the first embodiment. Furthermore, since each compartment encounters only one liquid component during a particular run, flushing either compartment of this embodiment is unneeded for repeated runs or for successive runs using the same solutions.

A common feature of both preferred embodiments is that the relatively large volume gradient generator also provides pulse damping to allow use of a reciprocating system pump.

Other advantages and features and a better understanding of the invention will be realized by reference the following detailed description in conjunction with the accompanying drawings.

DETAILED DESCRIPTION OF PREFERRED EMBODIMENTS

Figure 1:
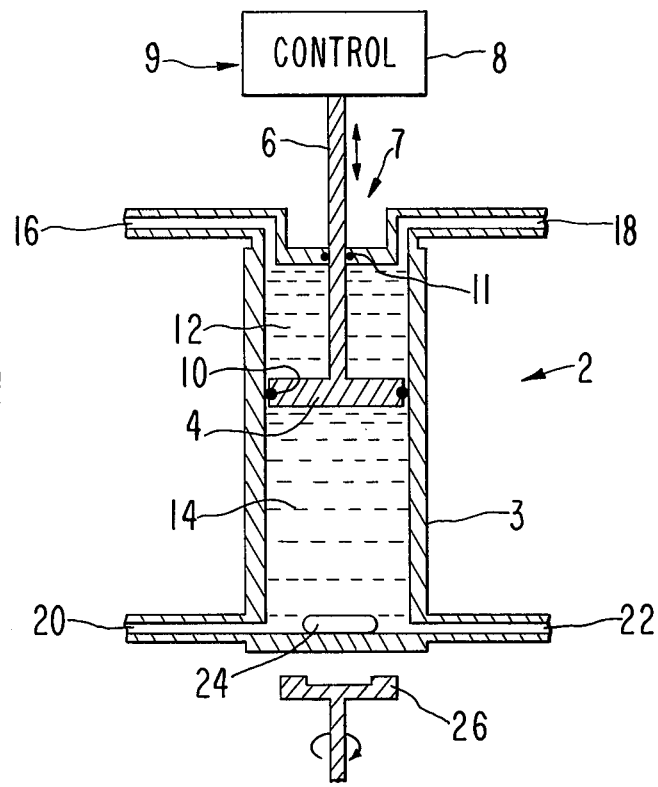
FIG. 1 is a cross sectional view of a preferred gradient generator according to one aspect of the invention.

Referring now to the drawings, there is depicted in FIG. 1 a preferred embodiment of a low cost, high pressure, constant volume flow rate solvent gradient generator shown 2. The gradient generating apparatus 2 comprises an enclosed vessel 3 having several pairs of input and output ports having openings sufficient to accommodate system flow. Piston means 7 is slidably contained within the vessel. The head 4 of piston means 7 and the bore of the vessel 3 provide first and second interior compartments 12 and 14, respectively. The instantaneous volumes of the respective compartments are defined by the instantaneous positioning of the piston. Input port 16 and output port 18 provide a flow path through the first compartment 12, while input port 20 and output port 22 provide a flow path through the second compartment 14. Compartments 12 and 14 are filled with mixture components or the final mixture in accordance with later described embodiments. Stirring means members 24 and 26 are provided for agitating fluid in the second compartment 14. Control means 8 responsive to operator inputs 9 controls the rate of movement of the piston means 7 within the vessel to so as to control compartment volumes.

The enclosed vessel 3, having a bore accessible by several input/output ports, is constructed preferably of chemically inert materials capable of withstanding relatively high pressure operation. Examples of such inert materials are stainless steel, Teflon (TFE or FEP), kel F, and glass. Seamless precision bore stainless steel tubing appears to be quite acceptable. Due in part to the low pressure seal, the expense of precision grinding the cylinder walls is eliminated.

Piston means 7 comprises a sliding shaft 6 coupled to the piston head 4. A high pressure Teflon O ring seal 11 of relatively small diameter is disposed between the piston shaft 6 and the top of the enclosed vessel. Disposition of the seal 11 in the upper housing provides ready access for tightening a conventional packing gland nut (not shown). The piston head 4 is circumscribed by a low pressure seal 10 such as a resilient Teflon coated rubber O ring or a flexible Teflon sealing ring. Seal 10 contacts the bore walls of the vessel 3 for sealing compartments 12 and 14 from one another so as to prevent mixture of the components contained in each compartment.

A conventional magnetic stirring means is provided for agitating the mixture in the second compartment 14. Magnetic member 26 disposed externally of the vessel 3 can be angularly displaced, causing the metallic stirring member 24 disposed withiin compartment 14 to rotate. Such agitation means is unnecessary, if the gradient generating apparatus is used in combination with a mixing chamber. See mixing chamber 33 in FIG. 3, discussed hereinafter.

The control means 8 comprises suitable drive means for controlling displacement of the piston means 7 within the vessel 3. Control means 8 may suitably comprise a motor driver which is speed controlled in accordance with time. Such controls are now well understood. Operator inputs 9 control the rate of displacement of the piston head 4, which controls compartment volumes and therefore the proportions of component mixtures, as will be subsequently explained. The input and output port openings are of sufficient size so as to accommodate flows generated over the entire Piston displacement range of the control means 8.

Specific dimensions of the gradient generating apparatus 2 are chosen in coordination with specific system function.

Figure 2:
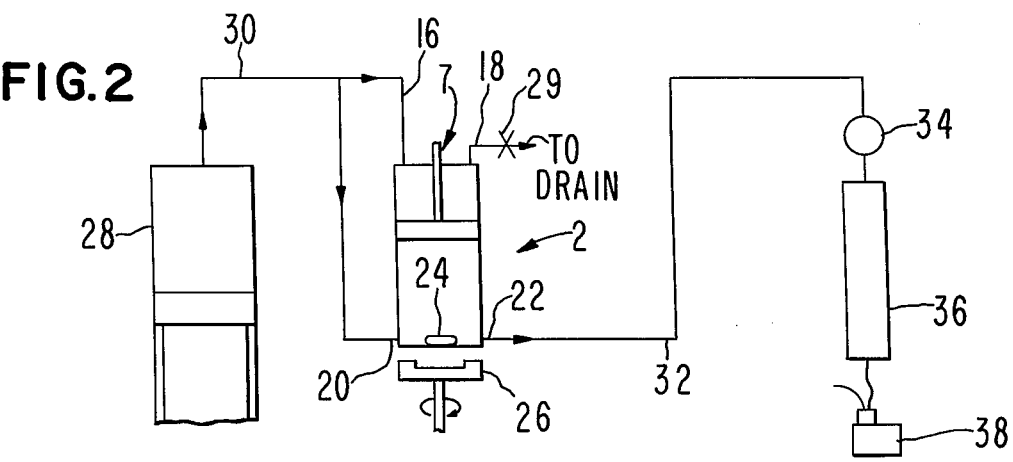
FIG. 2 depicts one embodiment of a chromatography system featuring the gradient generator of FIG. 1 in accordance with another aspect of the invention.

FIG. 2 depicts a chromatography system featuring the apparatus of FIG. 1 connected in a first preferred mode. A single high pressure pump 28, such as a Varian Model 8500 pump, is coupled via line 30 to the gradient generator 2. The output of the gradient generator 2 is coupled via means line 32 to a commercially available injector 34, which is coupled to column 36, which in turn is coupled to detector circuitry 38 for final analysis.

In the embodiment of FIG. 2, only specific ports are utilized. The output port 18 of the first compartment 12 is sealed by stopper means 29. Input port 16 of the first compartment 12 and input port 20 of the second compartment 14 are commonly coupled to receive the first component of the liquid mixture by way of line 30 from pump 28. The output port 22 of the second compartment 14 is coupled to provide a mixed solvent comprising the first component, which is introduced from the pump 28, and the second component, which is initially stored in compartment 14.

During initial operation of the chromatographic system of FIG. 2, the piston 7 is disposed at the top of the cylindrical vessel 3 at the start of the chromatographic run. The high pressure pump 28 supplies the first component to both compartments 12 and 14 where, compartment 14 is already previously filled with the second solvent component. High pressure pump 28 injects the first component into both compartment 12 and compartment 14 in accordance with piston, displacement. The piston is displaced downwardly from its initial position at a preselected rate, thereby increasing the volume of the first compartment 12 while decreasing the volume of the second compartment 14. Depending upon the selected rate of movement of the piston 7, more or less of the first solvent component from pump 28 will enter the first compartment 12, and less or more of the first solvent component will enter the second compartment 14. Because the total volume of liquid in the two compartments 12 and 14 is constant, the volume flow rate out of the vessel 3 through output port 22 of the second compartment 14 equals the sum of the volume flow rates into the input ports 16 and 20. The total volume flow is determined by the volume flow of the high pressure pump 28. As the first solvent component from pump 28 enters the second compartment 14, stirring means 26 thoroughly mixes the first and second solvent components.

The effect of the rate of displacement of the piston 7 on the composition of the mixed liquid flowing from output port 22 is seen from equation (1) below. Neglecting the cross sectional area of the piston shaft 6, which is small compared to the cross sectional area of the cylinder, and neglecting the volume of the stirring member 24, the volume of the second solvent component 14 initially in the second compartment at any point of time can be expressed as a fraction of the total volume of the first and second solvent components present in the second compartment 14 as follows:

$$\frac{V_A}{V_B + V_A} = \left[1 - \frac{\dot{x}}{L} t\right]^{\left(\frac{\dot{V}_p}{\dot{x}A} - 1\right)} \quad \text{EQN. (1)}$$

where equation (1) assumes a linear rate of descent, $\dot{x}$, for the piston of the term. $V_A$ is the volume of the second solvent component in the second compartment 14, and $V_B$ is the volume of the first solvent component in the second compartment 14, L is the inside length of the cylinder, A is the cross sectional area of the cylinder, $\dot{V}_p$ is the volume rate of flow of the first solvent component from the high pressure pump 28, and t is the time from the start of the gradient.

A study of equation (1) indicates that the liquid gradient generating apparatus according to FIG. 2 is capable of generating a wide range of gradient profiles. Three cases, namely, where $\dot{V}_p$ equals $\dot{x}A$, where $\dot{V}_p$ equals $2\dot{x}A$, and where $V_p/\dot{x}A$ is less than 2 and $V_p/\dot{x}A$ is greater than 2, are of special interest and characterize the system.

If the flow rate from the high pressure pump, $\dot{V}_p$, equals the product of the cross sectional area of the cylinder and the rate of displacement of the piston ($\dot{x}A$), the exponent in equation (1) is 0, and the solvent composition of the mixed liquid flowing from output port 22 is independent of time. Such a condition is commonly referred to as an isocratic operation. In other words, $V_B$ equals 0, and the entire volume of the first solvent component from the pump 28 is being input into the first compartment 12. Accordingly, only the second solvent component previously stored in the second compartment 14 is output via line 32.

If the flow rate from the high pressure pump 28 equals twice the volume swept out by the rate of displacement of the piston 7 times the cross sectional area of the cylinder, the exponent in equation (1) is unity and the gradient is linear with respect to time.

If the flow rate of the first solvent component from the high pressure pump 28 is less than twice the volume rate of displacement of the piston 7, then the exponent in equation (1) is less than unity, and the rate of change in composition in the second compartment 14 decreases with time. That is, less of the first component from the pump 28 enters the second compartment 14 as the chromatographic run progresses. Conversely, if the volume flow rate from the high pressure pump 28 is greater than twice the displacement rate of the piston 7, then the exponent in equation (1) is greater than unity and the rate of change of composition in the second compartment 14 increases with time. Accordingly, as the chromatographic run continues, an increasing amount of the first component from the pump 28 enters the second compartment to be mixed.

It is thus seen that a diverse range of gradients can be generated by the apparatus according to FIG. 2 using only a constant piston rate of displacement. Not requiring variance of the rate allows simpler control circuitry 8 (not shown) to be utilized than if the rate of displacement of the piston otherwise required varying.

Figure 3:
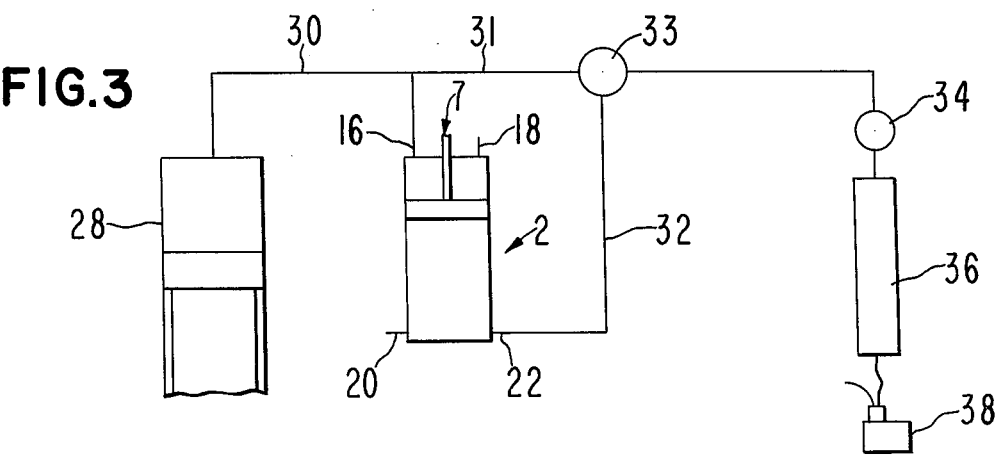
FIG. 3 depicts still another embodiment of a chromatography system featuring the gradient generating device of FIG. 1 in yet another aspect of the invention.

Referring now to FIG. 3, another chromatographic system is shown wherein the gradient generator according to FIG. 1 is utilized in a second configuration. Like components in FIGS. 2 and 3 have like reference numbers and will not be further discussed with respect to FIG. 3. The solvent gradient generator 2 in FIG. 3 is coupled to the high pressure pump 28 and to a mixing chamber 33.

In the embodiment of FIG. 3, the gradient generating apparatus 2 has both the output port 18 in the first compartment 12 and the input port 20 in the second compartment 14 sealed. Line 30 conveys the first solvent component from the pump 28 to a tee junction at which the first component divides and is controllably input into the first compartment 12 by way of input port 16 and into the mixing chamber 33 via line 31. Output port 22 of the second compartment 14 is coupled to the mixing chamber 33 by way of line 32.

Operation of the chromatographic system of FIG. 3 is as follows. Initially piston means 7 is displaced so as to minimize the volume of compartment 12 and to maximize the volume of compartment 14. The second compartment 14 is filled with the second solvent component to be mixed, while pump 28 introduces the first solvent component to be mixed. The control means 8 displaces the piston 7 downwardly at a controlled rate to control rate and proportion of mixture. The volume of the second solvent component in the mixture entering the injector 34 through the mixer 33, expressed as a fraction of the total volume of the first and second solvent components present in the second compartment 14, is characterized by equation (2) as follows:

$$V_A/V_A + V_B = \dot{x}A/\dot{V}_p \quad \text{EQN. (2)}$$

where the terms of equation (2) are the same as defined above in connection with equation (1). Analysis of EQN. (2) reveals that the mixing ratio within the chamber 33 is proportional to the rate of descent of the piston 7 in the cylinder. A linear rate of descent and a linear flow rate provide constant composition. By varying the rate of descent of the piston proportionally to the square of time, a linear gradient profile is generated. As with the earlier described embodiment, a diverse range of gradients is can be generated in accordance with specific movement of the piston means 7.

One advantage of the system of FIG. 3 is that flushing of the second compartment 14 is not required between runs. Each of the two compartments 12 and 14 in the gradient device is exposed to only one of the solvent components during the chromatographic run. Accordingly, when the gradient profile is repeated, or the same two solvent components are used during successive runs, the need to flush the two compartments of the gradient generating apparatus is obviated.

In each of the embodiments depicted in FIGS. 2 and 3, the pressures on the exposed areas of the two faces of the piston 7 are approximately equal. The opposing forces on the faces of the piston 7 thus tend to balance and cancel. Such equalization of pressures permits use of a low pressure seal 10 between the piston and the cylinder wall. The low pressure seal 10 allows use of a more flexible or resilient sealing member than if otherwise a high pressure seal were required. Use of such a flexible or resilient sealing member makes wall tolerances less critical. Furthermore, since the pressures are substantially equalized, the balance of force on the faces of the piston allows use of a low force driving mechanism 8 for driving the piston. The combination of relaxed wall tolerance and low driving force required to drive the piston reduces significantly the cost of the gradient generating apparatus.

Another advantage of the systems depicted in FIGS. 2 and 3 is the feature that a reciprocating type high pressure pump 28 may be utilized without the need for pulse damping means. As set forth in the introduction, a pulsating flow from a reciprocating pump is detrimental to the performance of liquid chromatography systems. However since reciprocating pumps are relatively inexpensive and are not limited to a finite reservoir, their use is economically and practically advantageous. The functions of the gradient generating apparatus 2 are therefore mutlifold, as it obviates the otherwise need for pulse damping apparatus.

It has been determined that an enclosed volume of liquid provides one of the more efficient types of pulse dampers in liquid chromatographic systems. In FIG. 2, the first compartment 12 in combination with the second compartment 14 provides the enclosed volume of liquid for pulse damping. In FIG. 3, the increasing volume of the first compartment 12 in the gradient generating apparatus 2 provides the enclosed volume of liquid. Furthermore, since the gradients are formed downstream of the pump 28 in both embodiments of FIG. 2 and FIG. 3, mixing effects within the pump 28 are negligible.

It will thus be appreciated that a new and improved solvent gradient generating apparatus has been provided for a liquid chromatographic system. Not only is only a single high pressure pump required in both embodiments, but a reciprocating type pump is suitably utilized, thereby effecting considerable economic savings. Furthermore, since the need for pulse damping apparatus has been obviated, additional savings are realized. By utilizing a system interconnect scheme which substantially equalizes pressure on both sides of the driving piston, a low pressure seal may be used thereby allowing still additional cost savings by making construction tolerances less critical.

It is understood that although the preferred generator has been described having only two compartments, additional compartments could be formed. That is, several heads could be provided on piston 7, with appropriate ports in the bore for mixing additional components. Similarly, generators as described could be connected in parallel for mixing additional components.

Although the invention has been described in its preferred form with a degree of particularity, it is understood that the present disclosure has been by way of example only. Numerous changes in the details of construction and the specific combination of the gradient generating apparatus with other components in a chromatographic system will be apparent without departing from the spirit and the scope of the invention as hereinafter claimed.

What is claimed is:

1. A liquid chromatography system having a controlled component solvent comprising:
    a. a pumping means for supplying under pressure a first solvent;
    b. a multi-compartmented solvent gradient generating means comprising a vessel having a substantially cylindrically configured bore, said vessel being adapted to have a second solvent in one said compartment, said one compartment having a first input port and a first output port, and another said compartment having a second input port and a second output port, first stopper means being provided for sealing said first input port, and second stopper means being provided for sealing said second output port;
    c. substantially cylindrically configured piston means, including sealing means, disposed within said bore and sealably extending outside said vessel, said piston means having a piston head slidably contained within said gradient generating means for defining in combination with said vessel said one compartment adjacent one side of said head and said another compartment adjacent the other side thereof;
    d. column means, including injector means, for selectively interacting said controlled component solvent with a stationary reactive element disposed within said column means;
    e. control means for controlling the rate of movement of said piston head within said bore; and
    f. mixing means coupling said first output port commonly with said second input port and with said pumping means for supplying said solvent having controlled component mixtures to said column means.

2. The chromatography system according to claim 1 and further including third stopper means for sealing said second output port, and including means commonly coupling said first input port and said second input port to said pumping means, said first output port being coupled to said injector means.

3. A liquid chromatograph system for providing a controlled mixture of a first liquid and a second liquid, said system comprising:
    a vessel having movable wall means for defining therewithin a first compartment and a second compartment;
    said second compartment, in operation of said system, being a container for said second liquid;

sealing means adjacent said movable wall means for isolating the contents of said second compartment from said first compartment;

each of said first and second compartments having an inlet port;

pump means for supplying said first liquid via a common conduit to said first and second compartments through the respective inlet ports thereof;

said second compartment having an outlet port; and control means for controllably moving said movable wall means, thereby causing a controlled mixture of said first and second liquids to flow out of said outlet port of said second compartment, the rate of flow of said mixture out of said second compartment being substantially determined by the rate of flow of said first liquid from said pump means.

4. The system of claim 3 wherein said vessel is of substantially cylindrical configuration, and said movable wall means comprises a piston head.

5. The system of claim 4 wherein said piston head is connected to a shaft slidably mounted within said first compartment, said shaft extending through an aperture in a fixed wall of said vessel to said control means.

6. The system of claim 5 further comprising high-pressure sealing means disposed adjacent said aperture in said fixed wall of said vessel in contact with said slidably mounted shaft to accommodate the pressure differential between the interior and the exterior of said first compartment.

7. The system of claim 6 wherein said high-pressure sealing means comprises an O-ring disposed circumjacent said shaft, said shaft being in sliding contact therewith.

8. The system of claim 4 wherein said sealing means adjacent said movable wall means comprises an O-ring affixed to said piston head in sliding contact with a fixed wall of said vessel.

9. The system of claim 3 wherein said second compartment, in operation of said system, can initially be filled with said second liquid.

10. The system of claim 3 wherein said sealing means adjacent said movable wall means comprises a low-pressure sealing means affixed to said movable wall means in contact with a fixed wall of said vessel to accommodate substantially equal pressures on either side of said movable wall means.

11. The system of claim 3 wherein said common conduit for supporting said first liquid from said pump means to said first and second compartments comprises a tee junction for dividing the outflow from said pump means into the inflow to said first compartment and the inflow to said second compartment.

12. The system of claim 3 further comprising stirring means disposed within said second compartment.

13. The system of claim 12 wherein said stirring means is metallic and is operated by a magnetic member disposed externally of said vessel.

14. The system of claim 3 wherein said control means is programmable to selectively provide a desired gradient from a range of gradients for one of said liquids in said mixture flowing out of said second compartment.

15. A liquid chromatograph system for providing a controlled mixture of a first liquid and a second liquid, a vessel having movable wall means for defining therewithin a first compartment and a second compartment;

said second compartment, in operation of said system, being a container for said second liquid;

sealing means adjacent said movable wall means for isolating the contents of said second compartment from said first compartment;

said first compartment having an inlet port;

a mixing chamber located externally of said vessel;

said mixing chamber having a first inlet port and a second inlet port;

pump means for supplying said first liquid via a common conduit to said first compartment of said vessel through said inlet port thereof and to said mixing chamber through said first inlet port thereof;

said second compartment having an outlet port;

means for providing liquid communication from said second compartment through said outlet port thereof to said mixing chamber through said second inlet port thereof;

said mixing chamber having an outlet port; and control means for controlling moving said movable wall means, thereby causing a controlled mixture of said first and second liquids to flow out of said outlet port of said mixing chamber, the rate of flow of said mixture out of said mixing chamber being substantially determined by the rate of flow of said first liquid from said pump means.

16. The system of claim 15 wherein said vessel is of substantially cylindrical configuration, and said movable wall means comprises a piston head.

17. The system of claim 16 wherein said piston head is connected to a shaft slidably mounted within said first compartment, said shaft extending through an aperture in a fixed wall of said vessel to said control means.

18. The system of claim 17 further comprising high-pressure sealing means disposed adjacent said aperture in said fixed wall of said vessel in contact with said slidably mounted shaft to accommodate the pressure differential between the interior and the exterior of said first compartment.

19. The system of claim 15 wherein said second compartment, in operation of said system, can initially be filled with said second liquid.

20. The system of claim 15 wherein said sealing means adjacent said movable wall means comprises a low-pressure sealing means affixed to said movable wall means in contact with a fixed wall of said vessel to accommodate substantially equal pressures on either side of said movable wall means.

21. The system of claim 15 wherein said common conduit for supplying said first liquid from said pump means to said first compartment of said vessel and to said mixing chamber comprises a tee junction for dividing the outflow from said pump means into the inflow to said first compartment port thereof.

22. The system of claim 15 wherein said control means is programmable to selectively provide a desired gradient from a range of gradients for one of said liquids in said mixture flowing out of said mixing chamber.

* * * * *

UNITED STATES PATENT AND TRADEMARK OFFICE
CERTIFICATE OF CORRECTION

PATENT NO. : 3,934,456
DATED : January 27, 1976
INVENTOR(S) : MINER M. MUNK

It is certified that error appears in the above-identified patent and that said Letters Patent are hereby corrected as shown below:

Column 3, line 49: Change "shown" to --indicated by reference number--.

Column 3, line 67: Change "to" to --3--.

Column 4, line 27: Change "withiin" to --within--.

Column 5, line 3: Change "where," to --, where--.

Column 5, line 7: Delete ",".

Column 5, line 33: Delete "14"; after "compartment" insert --14--.

Column 5, line 44: Change "of the" (first occurrence) to --7. The --; after "term" delete ".".

Column 7, line 4: Delete "is".

Column 9, line 49: Change "supporting" to --supplying--.

Column 10, line 23: Change "controlling" to --controllably--.

Signed and Sealed this

Thirty-first Day of August 1976

[SEAL]

Attest:

RUTH C. MASON
Attesting Officer

C. MARSHALL DANN
Commissioner of Patents and Trademarks